United States Patent
Pillow et al.

(10) Patent No.: US 9,353,130 B2
(45) Date of Patent: May 31, 2016

(54) PROCESS FOR THE IN SITU ACTIVATION OF ZINC METAL

(71) Applicants: CAMBRIDGE DISPLAY TECHNOLOGY LIMITED, Cambridgeshire (GB); SUMITOMO CHEMICAL COMPANY LIMITED, Tokyo (JP)

(72) Inventors: Jonathan Pillow, Baldock (GB); James Morey, Cambridge (GB)

(73) Assignees: CAMBRIDGE DISPLAY TECHNOLOGY LIMITED, Cambridgeshire (GB); SUMITOMO CHEMICAL COMPANY LIMITED, Tokyo (JP)

( * ) Notice: Subject to any disclaimer, the term of this patent is extended or adjusted under 35 U.S.C. 154(b) by 0 days.

(21) Appl. No.: 14/376,009

(22) PCT Filed: Jan. 30, 2013

(86) PCT No.: PCT/GB2013/000037
§ 371 (c)(1),
(2) Date: Jul. 31, 2014

(87) PCT Pub. No.: WO2013/114068
PCT Pub. Date: Aug. 8, 2013

(65) Prior Publication Data
US 2014/0371479 A1 Dec. 18, 2014

(30) Foreign Application Priority Data

Jan. 31, 2012 (GB) .................................. 1201660.6
Mar. 5, 2012 (GB) .................................. 1203827.9

(51) Int. Cl.
*C07F 3/06* (2006.01)
*C08G 61/12* (2006.01)
*C07C 45/61* (2006.01)
*H01L 51/00* (2006.01)
*H01L 51/50* (2006.01)

(52) U.S. Cl.
CPC . *C07F 3/06* (2013.01); *C07C 45/61* (2013.01); *C08G 61/12* (2013.01); *C07C 2103/22* (2013.01); *C08G 2261/124* (2013.01); *C08G 2261/148* (2013.01); *C08G 2261/1412* (2013.01); *C08G 2261/3142* (2013.01); *C08G 2261/3162* (2013.01); *C08G 2261/3245* (2013.01); *C08G 2261/411* (2013.01); *C08G 2261/95* (2013.01); *H01L 51/0035* (2013.01); *H01L 51/0039* (2013.01); *H01L 51/0043* (2013.01); *H01L 51/5012* (2013.01)

(58) Field of Classification Search
CPC ............ C07F 3/06; C07C 45/61; C08G 61/12
See application file for complete search history.

(56) References Cited

PUBLICATIONS

Boudet et al., "Directed Ortho Insertion (DoI): A New Approach to Functionalized Aryl and Heteroaryl Zinc Reagents," *J. Am. Chem. Soc.*, 129:12358-12359 (2007).
Fleckenstein et al., "Lithium Organozincate Complexes LiRZnX 2: Common Species in Organozinc Chemistry," *Organometallics*, 30(18):5018-5026 (2011).
Huo, "The Preparation of Alkylzinc Reagents from Unactivated Alkyl Bromides and Chlorides," *Org. Lett.*, 5(4):423-425 (2003).
Knochel et al., "Preparation and Reactions of Polyfunctional Organozinc Reagents in Organic Synthesis," *Chem. Rev.*, 93(6):2117-2188 (1993).
Knochel et al., "Product Class 1: Organometallic Complexes of Zinc," *Science of Synthesis, Category 1: Organometallics*, pp. 5-90 (2004).
Koszinowski et al., "Formation of Organozincate Anions in LiCl-Mediated Zinc Insertion Reactions," *Organometallics*, 28:771-779 (2009).
Metzger et al., "LiCl-Mediated Preparation of Highly Functionalized Benzylic Zinc Chlorides," *Org. Lett.*, 10(6):1107-1110 (2008).
Ren et al., "Highly Diastereoselective Synthesis of Homallylic Centers Using Substituted Allylic Zinc Reagents," *J. Am. Chem. Soc.*, 129(17):5376-5377 (2007).
Combined Search and Examination Report for Application No. GB1203827.9, dated Jun. 28, 2012.
International Preliminary Report on Patentability for Application No. PCT/GB2013/000037, dated Aug. 5, 2014.
International Search Report and Written Opinion for Application No. PCT/GB2013/000037, dated Aug. 5, 2013.

*Primary Examiner* — Sudhakar Katakam
(74) *Attorney, Agent, or Firm* — Marshall, Gerstein & Borun LLP

(57) ABSTRACT

A non-carcinogenic process for the activation of zinc metal in a medium polarity solvent, wherein said zinc metal is activated by the reaction thereof with a halogen and a lithium compound selected from lithium halides and lithium pseudohalides, the use of said activated zinc metal for the preparation of an organozinc halide of formula R—ZnX, and a process for the preparation of compounds obtainable by the reaction of said organozinc halide of formula R—ZnX with compounds having functionality enabling them to react with said organozinc halide.

19 Claims, No Drawings

PROCESS FOR THE IN SITU ACTIVATION OF ZINC METAL

SUMMARY OF THE INVENTION

The present invention relates to a process for the activation of zinc metal in a medium polarity solvent, wherein said zinc metal is activated by the combination thereof with a halogen and a lithium compound selected from lithium halides and lithium pseudohalides, to uses of said activated zinc metal in the preparation of organozinc halides and of the use of said organozinc halides in the preparation of organic compounds.

BACKGROUND OF THE INVENTION

The activation of zinc metal is important as unactivated zinc is generally unreactive and so activation is necessary for the preparation of organozinc reagents that are useful for the preparation of a number of different classes of compounds.

A number of techniques for the activation of zinc have been reported in the prior art. Metzeger et al. (Organic Letters, 2008, 10, 1107-1110) report activation of zinc dust (which is an optimum form of this reagent due to its high surface area) using a combination of 1,2-dibromoethane (classified as carcinogenic) and trimethylsilyl chloride. With added lithium chloride, this allows the formation of organozinc halides in tetrahydrofuran (THF) solution. The use of 1,2-dibromoethane, a carcinogen, makes this process practically disadvantageous.

Huo (Organic Letters, 2003, 3, 423-425) discloses the formation of organozinc halides using zinc metal of a variety of particle sizes in which a polar, aprotic, coordinating and nucleophilic solvent (such as N,N-dimethylacetamide) is used along with a sub-stoichiometric amount of iodine for activation. This avoids the problem associated with the process of Metzeger et al. of the use of a carcinogenic solvent. However, the very polar aprotic solvents used in the activation process such as N,N-dimethylacetamide can often hamper or react with the reactants or additives used in subsequent reactions of the organozinc halide. The strong dipole that enables the strong coordination properties of the solvent that make it effective at solvating the zinc complexes that are formed during the activation process can also cause a high nucleophilicity that can cause an unwanted reaction with an electrophile. For example, N,N-dimethylacetamide is well known to react with acid chlorides, which are common substrates for reactions with organozinc reagents.

It would therefore be a considerable advantage if these various problems that exist with the prior art zinc activation methods could be overcome. Firstly, any new method should not involve the activation of zinc dust using 1,2-dibromoethane or another carcinogen. Secondly, it is often desirable to separate the formed organozinc halide from excess zinc metal to prevent unwanted side-reactions in subsequent steps. Being able to use coarser zinc power/granules which can easily be separated from the zinc reagent would therefore be advantageous. Thirdly, a new methodology which would allow the use of less reactive solvents, typically of reduced polarity, would offer an advantage in reactions of the organozinc reagent where additives or other reactants could react with or be hampered by polar, aprotic solvents such as N,N-dimethylacetamide and would therefore overcome the limitations of the method described by Huo.

SUMMARY OF THE INVENTION

We have found that the addition of a halogen and a lithium halide or lithium pseudo halide to zinc metal enables excellent activation of zinc metal of a variety of particle sizes in a medium polarity solvent, allowing non-carcinogenic, efficient activation of zinc metal in a manner that can be performed on zinc granules that are of sufficient size to enable them to be readily separated after subsequent reaction of the activated zinc with an organohalide to form an organozinc halide.

Thus, in a first aspect of the present invention there is provided a process for the activation of zinc metal in a medium polarity solvent having a low nucleophilicity, wherein said zinc metal is activated by the reaction thereof with a halogen and a lithium compound selected from lithium halides and lithium pseudohalides.

In a preferred embodiment, the halogen is iodine.

Preferably, the solvent has a dielectric constant of from 3 to 40, more preferably 3 to 25. Furthermore, preferably it has low nucleophilicity as well.

In another preferred embodiment, the lithium compound is selected from lithium chloride, lithium bromide, lithium iodide, lithium trifluoromethanesulfonate, lithium cyanate and lithium isothiocyanate; and more preferably it is lithium chloride.

In another preferred embodiment, the activation of the zinc metal takes places in a solvent that does not react with any reagents or intermediates in the process. Examples of suitable solvents include tetrahydrofuran, diethyl ether, 1,4-dioxane, dichloromethane, ethyl acetate and acetonitrile and tetrahydrofuran is preferred.

In a second aspect of the present invention, there is provided a process for the preparation of an organozinc halide of formula R—ZnX, wherein R is an organo group and X is Cl, Br or I, preferably Br and the said process comprising the following steps:

(a) activation of zinc metal by the reaction thereof with a halogen and a lithium compound according to the first aspect of the present invention; and (b) reaction of the activated zinc moiety formed in step (a) with an organohalide of formula R—X to form said organozinc halide of formula R—ZnX.

Preferably, the organozinc halide of formula R—ZnX is a lithium halide additive of formula R—ZnBr.$(LiY^1)_n$ wherein $Y^1$ is a halide and n is an integer or non-integer number greater than zero or R—ZnX is a lithium pseudohalide additive of formula R—ZnBr.$(LiY^2)_n$ wherein $Y^2$ is a pseudohalide and n is defined as before; and more preferably it is a lithium halide additive of formula R—ZnBr.$(LiY^1)_n$ wherein $Y^1$ is chloride or bromide, preferably chloride and n is defined as before.

It is expected that in the presence of a lithium halide or lithium pseudohalide the organozinc halide will form an adduct or association with the lithium species to from a species that is closer in formula to R—ZnX.$(LiY^1)_n$, where typically n=1. The precise nature of the adduct between the organozinc halide and the lithium halide or pseudohalide is likely to vary according to the precise circumstances and species present, and could include an oligomeric or ion separated complex, as for example discussed in Organometallics 2011, 30, 5018-5026. The specific structures that are formed are not relevant to the claims of this invention and so the general description R—ZnX.$(LiY^1)_n$, will be used to denote all relevant structures.

Preferably, R is an alkyl group having from 1 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups, and where the specific nature of the optional substituents is known not to interfere substantially in an unwanted way with any of the chemistry or reactants that are added in subsequent steps.

We believe that the halogen, and preferably iodine, is key to the activation by exposing fresh zinc metal metal surface to the organohalide reagent. Furthermore, although not wishing to be bound by theory we believe that the lithium halide additive facilitates solubilisation of the resulting organozinc halide, transferring it from the metal surface into solution and thereby increasing the exposed surface area of the fresh zinc metal surface. The increased solubility of the complex with this lithium halide additive means that less polar and coordinating solvents, such as tetrahydrofuran, can be used.

In a third aspect of the present invention, there is provided a process for the preparation of a compound obtainable by the reaction of an organozinc halide of formula R—ZnX with a compound having functionality enabling it to react with said organozinc halide, wherein said organozinc halide of formula R—ZnX is prepared according to the process of the second aspect of the present invention.

Examples of such a process are provided below in the detailed description of the invention. Examples of compounds that can react with the organozinc reagent of the second aspect of the present invention and the compounds that are obtained as a result include but are not limited to acid chlorides (which give ketones); aryl halides (which give alkyl-substituted aryl compounds) and ketones (which give tertiary hydroxy alkyl compounds).

In a fourth aspect of the present invention, compounds obtained by the process of the third aspect of the present invention may be used as a monomer or as an intermediate for the preparation of a monomer for use in the preparation of a light emitting polymer.

In a fifth aspect of the present invention, there is provided an organic light emitting diode, wherein the organic light emitting layer comprises a light emitting polymer prepared according to the fourth aspect of the present invention.

DETAILED DESCRIPTION OF THE INVENTION

As noted above, the addition of a halogen and a lithium halide or lithium pseudo halide to zinc metal enables excellent activation of zinc metal of a variety of particle sizes in a medium polarity solvent, allowing non-carcinogenic, efficient activation of zinc metal in a manner that can be performed on zinc granules that are of sufficient size to enable them to be readily separated from the zinc reagent after completion of the reaction. Use of coarser zinc powder, granules or even larger particle size zinc metal enables it to be readily separated from the formed organozinc halide, thus preventing unwanted side reactions in subsequent steps.

In the process for the activation of zinc metal according to the first aspect of the present invention, in one embodiment the zinc metal is first mixed with the lithium compound, before the addition of the solvent to the resulting product and then finally the addition of said halogen. In a particularly preferred embodiment, the mixture resulting from the addition of said lithium compound to said zinc metal is dried before the addition of said solvent. In these preferred embodiments of the first aspect of the present invention, the mixture produced after the addition of said halogen is preferably heated to ensure more effective drying.

In another preferred embodiment of the present invention, the zinc metal is in the form of zinc dust, zinc powder, zinc granules, zinc shot, zinc wire, zinc sheets or some other macroscopic form of zinc metal, preferably zinc powder or zinc granules. The zinc metal has an average particle size of from $1 \times 10^{-3}$ to 25 mm, preferably, 0.01 to 20 mm, more preferably 0.05 to 10 mm and most preferably from 0.1 to 1 mm. The process of the present invention enables the use of much larger zinc metal such as zinc granules that can be easily separated from the zinc reagent, a considerable practical advantage.

Typically, the amount of iodine added is from 1 to 10 mol % of the amount of zinc metal.

The second aspect of the present invention utilises the activated zinc metal synthesised by the process according to the first aspect of the present invention to produce an organozinc halide by reaction with an organohalide reagent. As noted above, without wishing to be limited by any theory, we believe that the halogen is key to activation by exposing the fresh zinc metal surface to the organohalide reagent, with the lithium halide acting as an additive and facilitating solubilisation of the resulting organozinc halide, transferring it from the metal surface into solution.

The organozinc halides have utility in the synthesis of a number of different types of compounds, as discussed in greater detail below. Organozinc reagents have very wide applicability in industrial synthesis, due to their relative stability and high reaction selectivity—they can be used in the presence of a wide range of functional groups. The new process of preparing them in a simple and safe manner provided by the present invention therefore clearly offers wide benefits. It is expected that the procedure will be applicable to a wide range of alkyl halides and aryl halides.

As a reminder, in the second aspect of the present invention, there is provided a process for the preparation of an organozinc halide of formula R—ZnX, wherein R is an organo group and X is Cl, Br or I, preferably Br said process comprising the following steps:

(a) activation of zinc metal by treating it with a halogen and a lithium compound according to the first aspect of the present invention; and (b) reaction of the activated zinc moiety formed in step (a) with an organohalide of formula R—X to form said organozinc halide of formula R—ZnX. Preferably, the organozinc halide of formula R—ZnX is a lithium halide additive of formula R—ZnBr.$(LiY^1)_n$, wherein $Y^1$ is a halide and n is an integer or non-integer number greater than zero or R—ZnX is a lithium pseudohalide additive of formula R—ZnBr.$(LiY^2)_n$ wherein $Y^2$ is a pseudohalide and n is defined as before; and more preferably it is a lithium halide additive of formula R—ZnBr.$(LiY^1)_n$ wherein $Y^1$ is chloride or bromide, preferably chloride and n is defined as before.

Preferably, R is an optionally substituted alkyl group having from 1 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups, and where the specific nature of the optional substituents is known not to interfere substantially in any unwanted way with any of the chemistry or reactants that are added in subsequent steps.

More preferably, R is an optionally substituted alkyl group having from 1 to 20 carbon atoms, an optionally substituted alkenyl group having from 2 to 20 carbon atoms, an optionally substituted alkynyl group having from 2 to 20 carbon atoms or an optionally substituted aryl group selected from optionally substituted phenyl groups, naphthyl groups, fluorenyl groups, pyrenyl groups, anthracenyl groups, phenthrenyl groups, chrysenyl groups or naphthacenyl groups, wherein the optional substituents are selected from the group consisting of alkyl groups having from 1 to 15 carbon atoms, optionally substituted aryl groups having from 5 to 20 carbon atoms, haloalkyl groups having from 1 to 15 carbon atoms, carboxyl groups, amino groups, monoalkylamino groups wherein the alkyl groups have from 1 to 15 carbon atoms, dialkylamino groups wherein each alkyl group is the same or different and each is an alkyl group having from 1 to 15 carbon atoms, monoarylamino groups wherein the aryl group is optionally substituted and diarylamino groups wherein each aryl group is the same or different and is optionally substituted, with the expectation that the optional substituents are specifically chosen to not react with or interfere substantially in an unwanted manner with any other reagent or chemistry of subsequent reaction steps.

In one preferred embodiment of the second aspect of the present invention, steps (a) and (b) are performed consecutively in the same reaction vessel without isolation of the activated zinc intermediate and using the same solvent as used when zinc metal activation process.

In the third aspect of the present invention, as explained above there is provided a process for the preparation of a compound obtainable by the reaction of an organozinc halide of formula R—ZnX with a compound having functionality enabling it to react with said organozinc halide, wherein said organozinc halide of formula R—ZnX is prepared according to the process of the second aspect of the present invention.

In a first example of such a process, said compound obtainable by the reaction of an organozinc halide of formula R—ZnX with a compound having functionality enabling it to react with said organozinc halide is a ketone of formula R'—C(O)—R which is obtainable by the reaction of said organozinc halide with an acid chloride of formula R'C(O)—Cl in the presence of a Cu(I) salt. Preferably, the Cu(I) salt is CuCN.2LiCl.

Preferably, R' is an optionally substituted alkyl group having from 1 to 30 carbon atoms, an optionally substituted alkenyl group having from 2 to 30 carbon atoms, an optionally substituted alkynyl group having from 2 to 30 carbon atoms, an optionally substituted aryl group having from 5 to 20 carbon atoms having one or more aromatic rings, an optionally substituted saturated or partially unsaturated heterocyclic group containing at least one nitrogen, oxygen or sulphur atom which is a 4- to 8-membered saturated or partially unsaturated heterocyclic group having one or more rings (including bridged saturated or partially unsaturated heterocyclic groups having one or more rings) or a 5- to 7-membered heteroaryl group containing from 1 to 3 sulfur atoms, oxygen atoms and/or nitrogen atoms, wherein the optional substituents are selected from the group consisting of alkyl groups having from 1 to 20 carbon atoms, optionally substituted aryl groups having from 5 to 20 carbon atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, halo groups, carboxyl groups, cyano groups, nitro groups, amino groups, monoalkylamino groups wherein the alkyl groups have from 1 to 20 carbon atoms, dialkylamino groups wherein each alkyl group is the same or different and each is an alkyl group having from 1 to 20 carbon atoms and hydroxyl groups.

More preferably, R' is an optionally substituted alkyl group having from 1 to 20 carbon atoms, an optionally substituted alkenyl group having from 2 to 20 carbon atoms, an optionally substituted alkynyl group having from 2 to 20 carbon atoms, an optionally substituted aryl group selected from phenyl groups, naphthyl groups, fluorenyl groups, phenanthrenyl groups and anthracenyl groups or an optionally substituted heterocyclic group selected from furyl groups, thienyl groups, pyrrolyl groups and pyridyl groups, wherein the optional substituents are selected from the group consisting of alkyl groups having from 1 to 15 carbon atoms, optionally substituted aryl groups having from 5 to 20 carbon atoms, haloalkyl groups having from 1 to 15 carbon atoms, carboxyl groups, nitro groups, amino groups, monoalkylamino groups wherein the alkyl groups have from 1 to 15 carbon atoms, dialkylamino groups wherein each alkyl group is the same or different and each is an alkyl group having from 1 to 15 carbon atoms, monoarylamino groups wherein the aryl group is optionally substituted and diarylamino groups wherein each aryl groups is the same or different and is optionally substituted.

Preferably, said group of formula R is an optionally substituted alkyl group having from 1 to 30 carbon atoms, an optionally substituted alkenyl group having from 2 to 30 carbon atoms, an optionally substituted alkynyl group having from 2 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl groups is the same or different and is optionally substituted and hydroxyl groups, where the optional substituents that are present are known not to react with the chosen R'(CO)Cl compounds under the conditions of the reaction.

More preferably, said group of formula R is an optionally substituted alkyl group having from 1 to 20 carbon atoms, an optionally substituted alkenyl group having from 2 to 20 carbon atoms, an optionally substituted alkynyl group having from 2 to 20 carbon atoms or an optionally substituted aryl group selected from optionally substituted phenyl groups, naphthyl groups, fluorenyl groups, pyrenyl groups, phenanthrenyl groups, chrysenyl groups, anthracenyl groups and naphthacenyl groups, wherein the optional substituents are selected from the group consisting of alkyl groups having from 1 to 15 carbon atoms, optionally substituted aryl groups having from 5 to 20 carbon atoms, haloalkyl groups having from 1 to 15 carbon atoms, carboxyl groups, amino groups, monoalkylamino groups wherein the alkyl groups have from 1 to 15 carbon atoms and dialkylamino groups wherein each alkyl group is the same or different and each is an alkyl group having from 1 to 15 carbon atoms.

In a second example of the third aspect of the present invention, said compound obtainable by the reaction of an organozinc halide of formula R—ZnX with a compound having functionality enabling it to react with said organozinc halide is an alkyl-substituted aryl group of formula Ar—R, wherein Ar is an optionally substituted aryl group having from 5 to 20 carbon atoms having one or more aromatic rings, wherein the optional substituents are selected from the group consisting of alkyl groups having from 1 to 30 carbon atoms, optionally substituted aryl groups having from 5 to 20 carbon atoms, halogen atoms, haloalkyl groups having from 1 to 30 carbon atoms, alkoxy groups having from 1 to 30 carbon atoms, alkoxycarbonyl groups comprising carbonyl groups that are substituted by alkoxy groups having from 1 to 30 carbon atoms, carboxyl groups, cyano groups, nitro groups, amino groups, monoalkylamino groups wherein the alkyl groups have from 1 to 30 carbon atoms, dialkylamino groups wherein each alkyl group is the same or different and each is an alkyl group having from 1 to 30 carbon atoms, monoarylamino groups wherein the aryl group is optionally substituted, diarylamino groups wherein each aryl groups is the same or different and is optionally substituted and hydroxyl groups and R is as defined in the first example of the third aspect of the present invention, said compound of formula Ar—R being obtainable by the reaction of said organozinc halide with an aryl halide of formula Ar-Hal wherein Hal is a halogen atom.

Preferably, the reaction of said organozinc halide with said aryl halide of formula Ar-Hal is a Negishi cross-coupling performed using a nickel or palladium catalyst. Suitable examples of such a nickel catalyst include $Ni(PPh_3)_4$ and $Ni(PPh_3)_2Cl_2$, preferably $Ni(PPh_3)_2Cl_2$. Suitable examples of such a palladium catalyst include $Pd(OAc)_2$, $Pd(MeCN)_2Cl_2$ and $Pd_2(dba)_3$ wherein dba is a dibenzylideneacetone group.

In this second example of the third aspect of the present invention, Ar is preferably an optionally substituted aryl group selected from optionally substituted phenyl groups, naphthyl groups, fluorenyl groups, pyrenyl groups, phenanthryl groups, anthracenyl groups and naphthacenyl groups, wherein the optional substituents on said aryl group are selected from the group consisting of alkyl groups having from 1 to 20 carbon atoms, optionally substituted aryl groups having from 5 to 20 carbon atoms, haloalkyl groups having from 1 to 20 carbon atoms, carboxyl groups, nitro groups, amino groups, monoalkylamino groups wherein the alkyl groups have from 1 to 20 carbon atoms and dialkylamino groups wherein each alkyl group is the same or different and each is an alkyl group having from 1 to 20 carbon atoms, monoarylamino groups wherein the aryl group is optionally substituted, diarylamino groups wherein each aryl groups is the same or different and is optionally substituted; and more preferably it is an optionally substituted phenyl group wherein the optional substituents are selected from the group consisting of alkyl groups having from 1 to 15 carbon atoms, optionally substituted aryl groups having from 5 to 20 carbon atoms, haloalkyl groups having from 1 to 15 carbon atoms, carboxyl groups, nitro groups, amino groups, monoalkylamino groups wherein the alkyl groups have from 1 to 15 carbon atoms, dialkylamino groups wherein each alkyl group is the same or different and each is an alkyl group having from 1 to 15 carbon atoms, monoarylamino groups wherein the aryl group is optionally substituted and diarylamino groups wherein each aryl groups is the same or different and is optionally substituted.

In this second example of the third aspect of the present invention, R is preferably an optionally substituted alkyl group having from 1 to 30 carbon atoms, an optionally substituted alkenyl group having from 2 to 30 carbon atoms, an optionally substituted alkynyl group having from 2 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, amino groups, monoalkylamino groups wherein the alkyl groups have from 1 to 20 carbon atoms, dialkylamino groups wherein each alkyl group is the same or different and each is an alkyl group having from 1 to 20 carbon atoms and hydroxyl groups. More preferably it is an optionally substituted alkyl group having from 1 to 15 carbon atoms, an optionally substituted alkenyl group having from 2 to 15 carbon atoms, an optionally substituted alkynyl group having from 2 to 15 carbon atoms or an optionally substituted aryl group selected from optionally substituted phenyl groups, naphthyl groups, fluorenyl groups, phenanthrenyl groups, pyrenyl groups, anthracenyl groups and naphthacenyl groups, wherein the optional substituents on said aryl group are selected from the group consisting of alkyl groups having from 1 to 15 carbon atoms, optionally substituted aryl groups having from 5 to 20 carbon atoms, haloalkyl groups having from 1 to 15 carbon atoms, carboxyl groups, amino groups, monoalkylamino groups wherein the alkyl groups have from 1 to 15 carbon atoms and dialkylamino groups wherein each alkyl group is the same or different and each is an alkyl group having from 1 to 15 carbon atoms.

In a third example of the third aspect of the present invention, said compound obtainable by the reaction of an organozinc halide of formula R—ZnX with a compound having functionality enabling it to react with said organozinc halide is an alcohol of formula R'—C(R")(OH)—R, said compound that reacts with said organozinc halide having the formula R'—C(O)—R".

In this third example of the third aspect of the present invention, R' is preferably as defined for the same group in the second example above and R is as defined for the same group in the first example of the third aspect of the present invention. This applies to both the broadest definitions of the groups and the preferred definitions of said groups.

In this third example of the third aspect of the present invention, R" is a hydrogen atom, an optionally substituted alkyl group having from 1 to 30 carbon atoms, an optionally substituted alkenyl group having from 2 to 30 carbon atoms, an optionally substituted alkynyl group having from 2 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, nitro groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl groups is the same or different and is optionally substituted and hydroxyl groups.

Preferably, R" is a hydrogen atom, an optionally substituted alkyl group having from 1 to 15 carbon atoms, an optionally substituted alkenyl group having from 2 to 15 carbon atoms, an optionally substituted alkynyl group having from 2 to 15 carbon atoms or an optionally substituted aryl group selected from optionally substituted phenyl groups, naphthyl groups, fluorenyl groups, pyrenyl groups, phenanthrenyl groups, anthracenyl groups and naphthacenyl groups, wherein the optional substituents on said aryl group are selected from the group consisting of alkyl groups having from 1 to 15 carbon atoms, optionally substituted aryl groups having from 5 to 20 carbon atoms, haloalkyl groups having from 1 to 15 carbon atoms, carboxyl groups, nitro groups, amino groups, monoalkylamino groups wherein the alkyl groups have from 1 to 15 carbon atoms, dialkylamino groups wherein each alkyl group is the same or different and each is an alkyl group having from 1 to 15 carbon atoms, monoarylamino groups wherein the aryl group is optionally substituted and diarylamino groups wherein each aryl groups is the same or different and is optionally substituted.

In a fourth example of the third aspect of the present invention, said compound obtainable by the reaction of an organozinc halide of formula R—ZnX with a compound having functionality enabling it to react with said organozinc halide is an amine of formula (I):

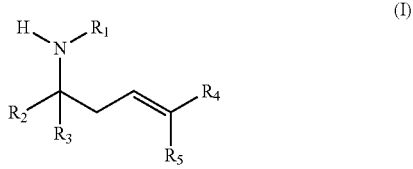

(I)

wherein:

R is as defined in the first example of the third aspect of the present invention;

$R_1$ and $R_2$ are the same or different and each can be an optionally substituted alkyl group having from 1 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, halogen atoms, optionally substituted aryl groups having from 5 to 20 carbon atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, nitro groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups;

$R_3$ is a hydrogen atom or an alkyl group having from 1 to 20 carbon atoms; and $R_4$ and $R_5$ are the same or different and each can be an optionally substituted alkyl group having from 1 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, cyano groups, nitro groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups; said compound that reacts with said organozinc halide of formula R—ZnX being an imine of formula (II):

(II)

wherein $R_1$, $R_2$ and $R_3$ are as defined above; and the organozinc halide of formula R—ZnX is a group of formula (III):

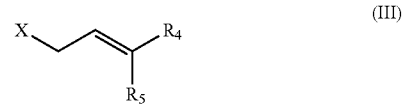

(III)

wherein $R_4$ and $R_5$ are as defined above, R is as defined in the first example of the third aspect of the present invention and X is bromine or iodine, preferably bromine.

In a preferred embodiment of the fourth example of the third aspect of the present invention:

$R_1$ and $R_2$ are the same or different and each can be an optionally substituted alkyl group having from 1 to 15 carbon atoms or an optionally aryl group selected from optionally substituted phenyl groups, naphthyl groups, fluorenyl groups, pyrenyl groups, phenanthrenyl groups, anthracenyl groups and naphthacenyl groups, wherein the optional substituents on said aryl group are selected from the group consisting of alkyl groups having from 1 to 15 carbon atoms, optionally substituted aryl groups having from 5 to 20 carbon atoms, halogen atoms, haloalkyl groups having from 1 to 15 carbon atoms, alkoxy groups having from 1 to 15 carbon atoms, cyano groups, nitro groups, amino groups, monoalkylamino groups wherein the alkyl groups have from 1 to 15 carbon atoms, dialkylamino groups wherein each alkyl group is the same or different and each is an alkyl group having from 1 to 15 carbon atoms, monoarylamino groups wherein the aryl group is optionally substituted, diarylamino groups wherein each aryl group is the same or different and is optionally substituted and hydroxyl groups;

$R_3$ is a hydrogen atom or an alkyl group having from 1 to 15 carbon atoms; and $R_4$ and $R_5$ are the same or different and each can be an optionally substituted alkyl group having from 1 to 15 carbon atoms or an optionally aryl group selected from optionally substituted phenyl groups, naphthyl groups, fluorenyl groups, phenanthrenyl groups, chrysenyl groups, pyrenyl groups, anthracenyl groups and naphthacenyl groups, wherein the optional substituents on said aryl group are selected from the group consisting of alkyl groups having from 1 to 15 carbon atoms, optionally substituted aryl groups having from 5 to 20 carbon atoms, halogen atoms, haloalkyl groups having from 1 to 15 carbon atoms, alkoxy groups having from 1 to 15 carbon atoms, cyano groups, nitro groups, amino groups, monoalkylamino groups wherein the alkyl groups have from 1 to 15 carbon atoms, dialkylamino groups wherein each alkyl group is the same or different and each is an alkyl group having from 1 to 15 carbon atoms, monoarylamino groups wherein the aryl group is optionally substituted, diarylamino groups wherein each aryl group is the same or different and is optionally substituted and hydroxyl groups.

In a fourth aspect of the present invention, there is provided use of compounds obtainable according to the third aspect of the present invention, such as those shown in the four examples of this third aspect above, as a monomer or as an intermediate for the preparation of a monomer for use in the preparation of a light emitting polymer.

In a fifth aspect of the present invention, as previously noted, there is provided an organic light emitting diode, wherein the organic light emitting layer comprises a light emitting polymer prepared according to the fourth aspect of the present invention.

As can be seen from the above, the organozinc reagent obtainable in the second aspect of the present invention from the activated zinc metal obtainable in the process of the first aspect of the invention is particularly useful, enabling the synthesis of a wide range of important compounds. Ketones are readily accessible from these organozinc reagents and acid chlorides in the presence of a Cu(I) salt. This approach is widely applicable, as can be seen from the above examples in the third aspect of the present invention. Alternative uses of this technology include a wide scope for the use of this methodology. Examples above include zinc- and palladium-catalysed C—C bond forming reactions, such as Negishi coupling to prepare substituted alkyl-substituted aryl compounds. Similarly, with judicious choice of additives, chemoselective addition to a broad range of carbonyl-containing intermediates allows access to a wide range of compound types interchangeable by standard functional group transformations, such as the formation of tertiary alcohols as shown above. Boron trifluoride can activate aldehydes to react with zinc reagents. Another example is the preparation of β-aminoalkenes from imines and organozinc compounds formed from β-aminoalkenyl halides. Further examples of the reactions of organozincates that are described in the literature are also expected to benefit from the activation process described herein.

EXAMPLE 1

Synthesis of 3-Hexyl-1-(4'-bromophenyl)nonan-1-ones

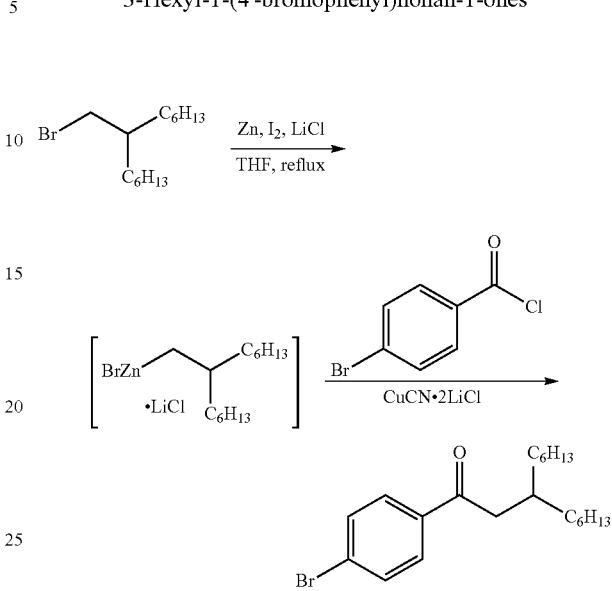

(a) Preparation of 2-hexyl-1-octylzinc bromide

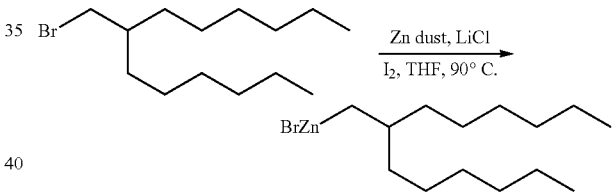

A mixture of zinc dust (1.91 g, 29.9 mmol) and lithium chloride (1.35 g, 31.8 mmol) was heated strongly under vacuum for about 10 minutes. After cooling to room temperature, the flask was filled with nitrogen and iodine (0.294 g, 1.16 mmol) added. The solid mixture was stirred for 5 minutes before the addition of dry THF (20 mL). The slurry was heated to 90° C. and then 2-hexyl-1-bromooctane added in a single portion (5.0 g, 18 mmol) with the progress of zinc insertion monitored by GC-MS of a quenched aliquot. After approximately 48 hours heating, zinc insertion was shown to be approximately 95% complete.

(b) Preparation of CuCN.2LiCl

A mixture of lithium chloride (1.68 g, 39.6 mmol) and copper (I) cyanide (1.77 g, 19.8 mmol) was heated under vacuum at 160° C. for 5 hours. After cooling to room temperature, the flask was filled with nitrogen and the solids dissolved by the addition of dry THF (50 mL) with stirring. The light brown solution was cooled in an ice/sodium chloride/water bath.

(c) Formation of the Zn—Cu Complex and Addition of the Benzoyl Chloride to Give 3-hexyl-1-phenylnonan-1-one

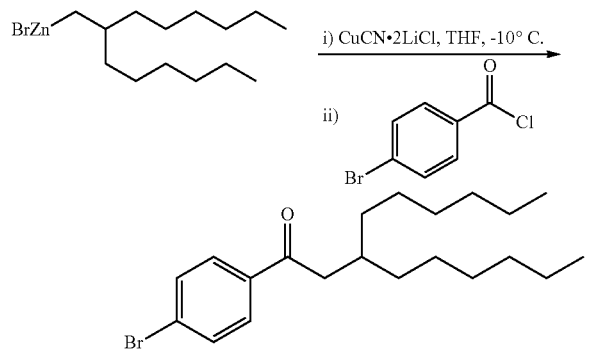

The zincate slurry prepared in step (a) was added to the cold solution of CuCN.2LiCl and the grey mixture stirred for 15 minutes. A solution of 4-bromobenzoyl chloride (3.16 g, 14.4 mmol) in dry THF (10 mL) was added drop-wise quickly and the mixture was allowed to warm to ambient temperature over approximately 48 hours. The brown suspension was filtered through a plug of silica with copious washing with THF. The pale yellow filtrate was treated with a solution of alkaline sodium hypochlorite (400 mL) and stirred for approximately 1 hour. Additional sodium hypochlorite (100 mL) was added resulting in a colour change from blue to brick red. The aqueous solution was extracted with diethyl ether and the combined organic extracts were dried over anhydrous magnesium sulphate, filtered and concentrated to dryness to give a brown oil. Approximately equal volumes of methanol and hexane were added to the oily residue and concentrated under strong vacuum to give a brown oil which partially precipitated. Addition of hexane gave a slurry which was filtered under suction to remove a beige solid inorganic residue. The hexane filtrate was loaded onto a Biotage 100 g SNAP KP-Sil cartridge and eluted using a 0 to 50% dichloromethane in hexane gradient. 3-Hexyl-1-phenylnoanan-1-one was isolated as a dark amber oil (3.56 g, 68%) which contained an unknown minor impurity.

GC-MS: Retention time=11.38 minutes gives m/z=295, 297 (fragment)

$^1$H NMR (600 MHz, CDCl$_3$): δ=7.81 (d, 2H, J=8.6 Hz), 7.59 (d, 2H, J=8.6 Hz), 2.83 (2H, d, J=6.7 Hz), 2.05 (br. multiplet, 1H), 1.36-1.20 (br. multiplet, 22H), 0.86 (t+impurity, 7H, J=6.9 Hz).

$^{13}$C{$^1$H} NMR (125 MHz, CDCl$_3$): δ=199.8, 136.2, 131.8, 129.7, 127.9, 43.5, 34.4, 34.1, 31.9, 29.6, 26.7, 22.7, 14.1 (some minor impurity signals present).

EXAMPLE 2

Synthesis of 3-Hexyl-1-(2',7'-dibromo-9',9'-diphenylfluoren-4'-yl)nonan-1-one

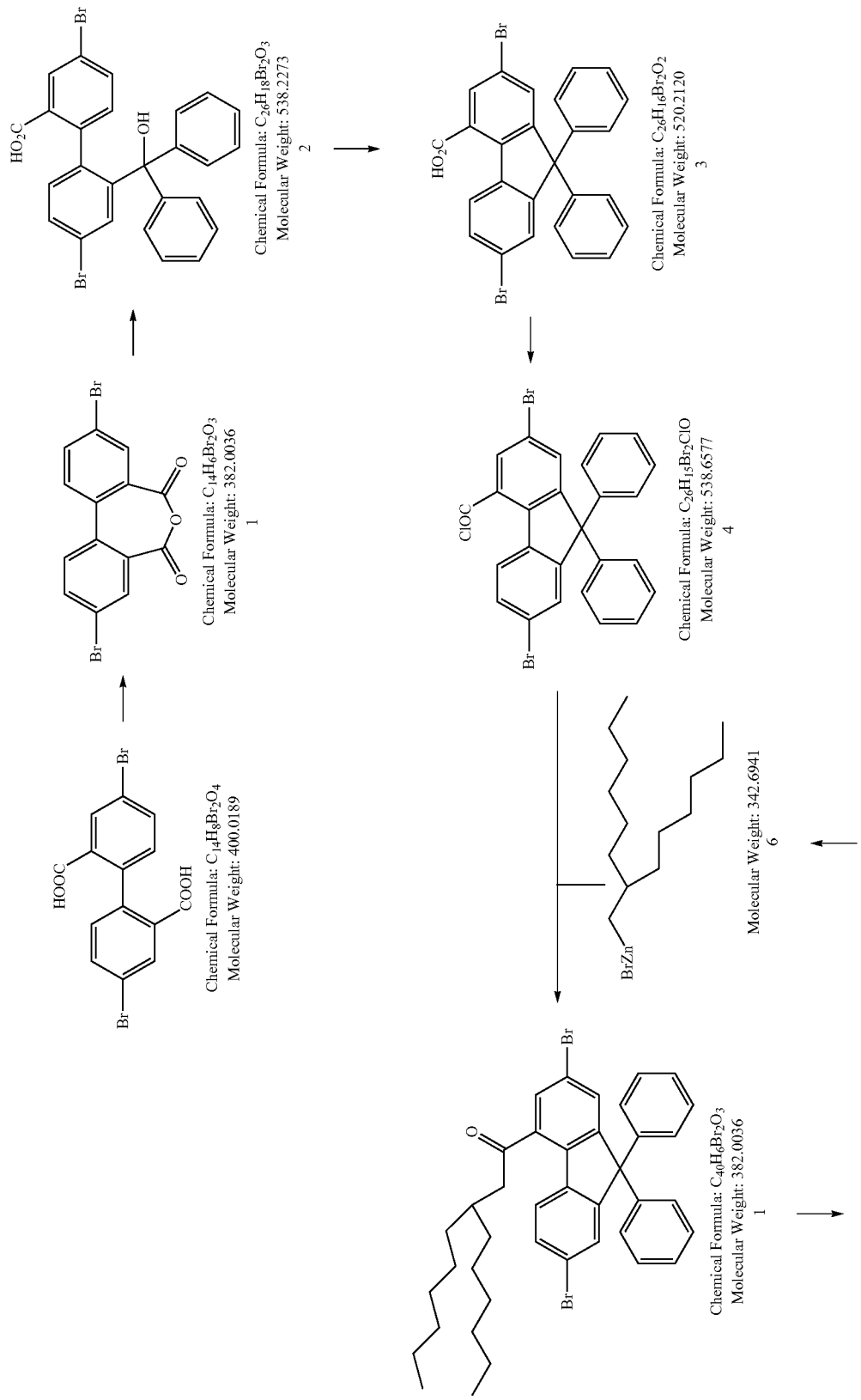

-continued
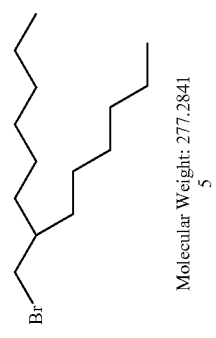
Molecular Weight: 277.2841
5
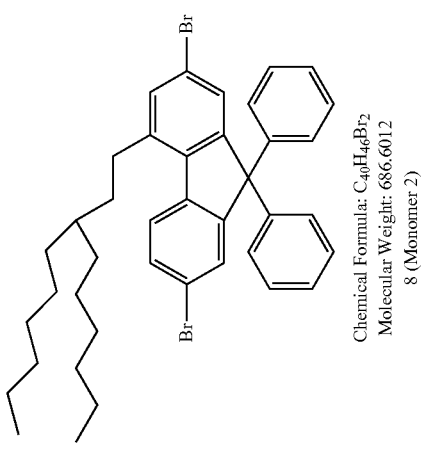
Chemical Formula: $C_{40}H_{46}Br_2$
Molecular Weight: 686.6012
8 (Monomer 2)

Compound 1:

Acetic anhydride (408.36 g, 4 mol) was added to 4,4'-Dibromodiphenic acid (400 g, 1 mol). The resulting slurry was stirred and heated under reflux overnight and then cooled to 60° C. Acetic acid (600 ml) was added and the stirred mixture was heated under reflux for 1 h and then cooled to room temperature. The resulting brown solid was filtered off, washed with acetonitrile and dried in a vacuum oven (50° C., ca. 2 days) to yield compound 1 (368.42 g, 96%) as a brown solid.

Compound 2:

Phenyl lithium (346.1 ml, 1.8 M in di-n-butyl ether, 0.623 mol) was added dropwise to a stirred, cooled (−78° C.) solution of compound 1 (119 g, 0.312 mol) in anhydrous THF (1.5 L) under dry nitrogen. The reaction mixture was stirred for ca. 2 h and then warmed to room temperature, stirring overnight. The reaction mixture was then cooled in an ice/water bath and water (200 ml) was added dropwise and the mixture was concentrated under vacuum to yield a dark brown waxy solid. The solid was dissolved in diethyl ether and washed twice with water, the aqueous components were extracted with diethyl ether, the combined organic extracts were dried over anhydrous $MgSO_4$ and the solvent was removed under vacuum to yield a brown oil. The oil was stirred in hydrochloric acid (2M aqueous solution) which afforded a brown precipitate which was filtered and triturated (hexane). This process yielded a brown solid, which was used in the next stage without further purification.

Compound 3:

Chlorobenzene (750 ml) was added to compound 2 (160 g, 0.297 mol) to give a light brown slurry. Trifluoroacetic acid (750 ml) was added to the stirred mixture (giving an immediate colour change from light brown to black) and all remaining material dissolved. The stirred mixture was heated under reflux for 2 days then cooled to room temperature. Water (300 ml) was added to quench the reaction. The product was extracted into ethyl acetate (5×500 ml), washed with water and the aqueous extracts were extracted with a further portion of ethyl acetate. The combined organic extracts were dried over anhydrous $MgSO_4$ and the solvent was removed under vacuum to yield compound 3 as a solid (139.06 g, 90%).

Compound 4:

Compound 3 (139 g, 0.267 mol) was dissolved in dry toluene (1 L) under an atmosphere of dry nitrogen with vigorous stirring. Thionyl chloride (33.6 ml, 0.452 mol) was added and the stirred mixture was heated under reflux for 24 h, with evolution of hydrogen chloride. The mixture was cooled to room temperature and the toluene and excess thionyl chloride was removed by vacuum distillation to yield a brown solid, which was used without further purification.

Compound 6:

Zinc granules (32.93 g, 0.504 mol) and lithium chloride (21.35 g, 0.504 mol) were heated to 165° C. under vacuum with vigorous stirring for 90 mins and then an atmosphere of dry nitrogen was introduced. Iodine (4.26 g, 16.8 mmol) and dry THF (500 ml) were then added to the stirred mixture, which immediately formed a brown solution that decolourised over 10 mins. The mixture was heated under reflux and 7-bromomethyltridecane (5, 93 g, 0.336 mol) was added in a single portion. Heating was continued for ca. 65 h, GCMS revealed a complete reaction had occurred. The material was used in subsequent stages without purification.

Compound 7:

Copper cyanide (33.1 g, 0.370 mol) and lithium chloride (31.3 g, 0.738 mol) were heated to 165° C. under vacuum with vigorous mixing for 5 h. The stirred mixture was cooled to room temperature, dry THF (500 ml) was added and the mixture cooled (ice/salt bath) for 15 mins. Compound 6 (0.336 mol, assumed) was added by cannula and the mixture was stirred for 15 mins. Compound 4 (0.267 mol, assumed) was added to the mixture rapidly by cannula and the stirred mixture was allowed to warm to room temperature overnight. Sodium hydroxide (aq. 10% w/v, ca. 500 ml) was added to the mixture which was stirred together for 5 mins, before the THF was removed under vacuum. The product was extracted into hexane (ca. 1 L) and the mixture separated. The organic phase was stirred over bleach for 1 h, the organic phase was separated, dried over anhydrous $MgSO_4$ and the solvent removed under vacuum. The resulting solid was passed through a plug of silica (hexane, with increasing volume fractions of DCM to elute) to yield an orange oil (87 g, 46%). LCMS revealed the presence of analogous methyl ester (ca. 19%) and esters of compound 5 (ca. 5%), which could not be easily separated. The mixture was carried forward without further purification.

Compound 8:

Trifluoroacetic acid (350 ml, 3.78 mol) was added to compound 7 (85 g, 0.121 mol) and the mixture was stirred. Triethylsilane (100 ml, 2.4 mol) was added to the mixture which was stirred together overnight. TLC revealed an incomplete reaction, so additional triethylsilane (40 ml) was added, the mixture was heated to 60° C. and the reaction continued for a further 2 h. The temperature was increased to 70° C. and the reaction continued overnight. The resulting precipitate was filtered and washed with water and acetonitrile. The solid was then passed though a plug of silica (10% DCM/hexane) and then recrystallised from hexane/acetonitrile. The resulting solid was recrystallised twice from ethyl acetate/IPA, toluene/methanol and toluene/acetonitrile and then dissolved in DCM and precipitated from methanol to yield compound 8 as a colourless solid (29.69 g, 36%, 99.7% purity by HPLC).

POLYMER EXAMPLE 1

A polymer was prepared by Suzuki polymerisation as described in WO 00/53656 of the following monomers:

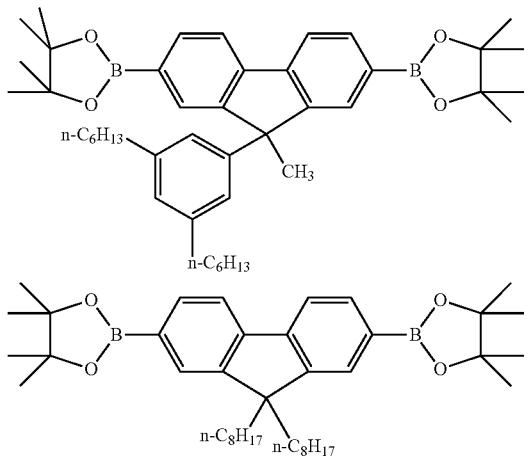

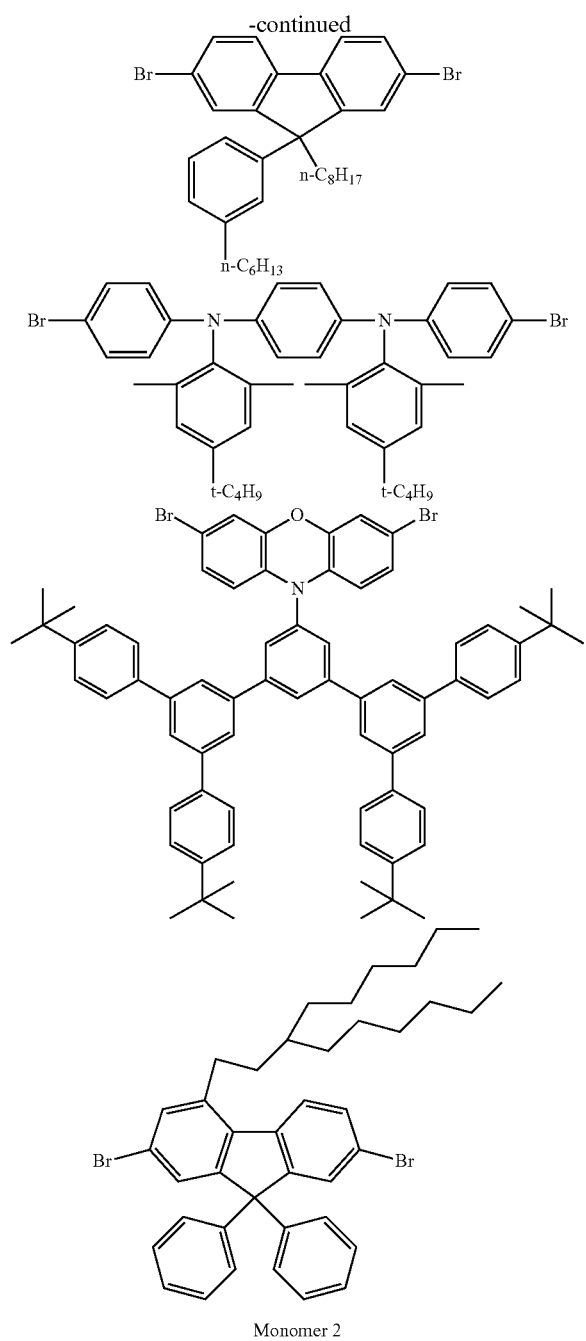

Monomer 2

The invention claimed is:

1. A process for activating zinc metal, comprising:
providing zinc metal in a medium polarity solvent having a low nucleophilicity; and
reacting said zinc metal with a halogen and a lithium compound selected from lithium halides and lithium pseudohalides, thereby activating said zinc metal,
wherein the medium polarity solvent having low nucleophilicity is selected from the group consisting of tetrahydrofuran, diethyl ether, any other symmetric or asymmetric, cyclic or acyclic, substituted or unsubstituted dialkylether, dichloromethane, and ethyl acetate, with the proviso that the solvent chosen must not react with or interfere in an unwanted manner with any subsequent reagent or chemical process.

2. A process according to claim 1, wherein said zinc metal is first mixed with said lithium compound, before the addition of said solvent to the resulting product and then finally the addition of said halogen.

3. A process according to claim 2, wherein the mixture resulting from the addition of said lithium compound to said zinc metal is dried before the addition of said solvent.

4. A process according to claim 2, wherein the mixture produced after the addition of said halogen is heated.

5. A process according to claim 1, wherein said lithium compound is selected from lithium chloride, lithium bromide, lithium iodide, lithium trifluoromethanesulfonate, lithium cyanate and lithium isothiocyanate.

6. A process according to claim 1, wherein said halogen is iodine.

7. A process according to claim 1, wherein said zinc metal is in the form of zinc dust, zinc powder, zinc granules, zinc shot, zinc wire, zinc sheets or other macroscopic form of zinc.

8. A process according to claim 1, wherein said zinc metal has an average particle size of from $1\times10^{-3}$ to 10 mm.

9. A process according to claim 6, wherein the amount of iodine added is from 1 to 10 mol % of the amount of zinc metal.

10. A process for the preparation of an organozinc halide of formula R—ZnX, wherein R is an organo group and X is Cl, Br or I, said process comprising the following steps:
(a) activation of zinc metal by the treatment thereof with a halogen and a lithium compound according to claim 1; and
(b) reaction of the activated zinc moiety formed in step (a) with an organohalide of formula R—X to form said organozinc halide of formula R—ZnX.

11. A process according to claim 10, wherein said organozinc halide of formula R—ZnX is a lithium halide additive of formula R—ZnBr.$(LiY^1)_n$ wherein $Y^1$ is a halide and n is an integer or non-integer number greater than zero or R—ZnX is a lithium pseudohalide additive of formula R—ZnBr.$(LiY^2)_n$ wherein $Y^2$ is a pseudohalide and n is an integer or non-integer number greater than zero.

12. A process according to claim 10, wherein R is an optionally substituted alkyl group having from 1 to 30 carbon atoms, an optionally substituted alkenyl group having from 2 to 30 carbon atoms, an optionally substituted alkynyl group having from 2 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups.

13. A process according to claim 10, wherein steps (a) and (b) are performed consecutively in the same reaction vessel without isolation of the activated zinc intermediate and using the same solvent as used for the zinc metal activation process.

14. A process for the preparation of a compound obtainable by the reaction of an organozinc halide of formula R—ZnX with a compound having functionality enabling it to react with said organozinc halide, wherein said organozinc halide of formula R—ZnX is prepared according to the process according to claim 10.

15. A process according to claim 14, wherein said compound obtainable by the reaction of an organozinc halide of formula R—ZnX with a compound having functionality enabling it to react with said organozinc halide is a ketone of formula R'—C(O)—R obtainable by the reaction of said organozinc halide with an acid chloride of formula R'C(O)—Cl in the presence of a Cu(I) salt.

16. A process according to claim 14, wherein said compound obtainable by the reaction of an organozinc halide of formula R—ZnX with a compound having functionality enabling it to react with said organozinc halide is an alkyl-substituted aryl group of formula Ar—R, wherein Ar is an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, nitro groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups and R is an organo group, said compound of formula Ar—R being obtainable by the reaction of said organozinc halide with an aryl halide of formula Ar-Hal wherein Hal is a halogen atom.

17. A process according to claim 14, wherein said compound obtainable by the reaction of an organozinc halide of formula R—ZnX with a compound having functionality enabling it to react with said organozinc halide is an alcohol of formula R'—C(R")(OH)—R, said compound that reacts with said organozinc halide having the formula R'—C(O)—R".

18. A process according to claim 17, wherein the reaction of said organozinc halide of formula R—ZnX with said compound of formula R'—C(O)—R" is performed in the presence of boron trifluoride.

19. A process according to claim 14, wherein said compound obtainable by the reaction of an organozinc halide of formula R—ZnX with a compound having functionality enabling it to react with said organozinc halide is a primary amine of formula (I):

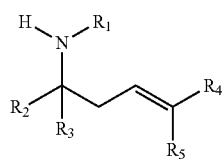

wherein:
R is an optionally substituted alkyl group having from 1 to 30 carbon atoms, an optionally substituted alkenyl group having from 2 to 30 carbon atoms, an optionally substituted alkynyl group having from 2 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups;

$R_1$ and $R_2$ are the same or different and each can be an optionally substituted alkyl group having from 1 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, alkoxycarbonyl groups comprising carbonyl groups that are substituted by alkoxy groups having from 1 to 20 carbon atoms, carboxyl groups, cyano groups, nitro groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups;

$R_3$ is a hydrogen atom or an alkyl group having from 1 to 20 carbon atoms; and $R_4$ and $R_5$ are the same or different and each can be an optionally substituted alkyl group having from 1 to 30 carbon atoms or an optionally substituted aryl group having from 5 to 20 carbon atoms having one or more aromatic rings, wherein the optional substituents are selected from the group consisting of alkyl groups having from 1 to 20 carbon atoms, optionally substituted aryl groups having from 5 to 20 carbon atoms, halogen atoms, haloalkyl groups having from 1 to 20 carbon atoms, alkoxy groups having from 1 to 20 carbon atoms, cyano groups, nitro groups, amino groups, monoalkylamino groups wherein the alkyl groups have from 1 to 20 carbon atoms, dialkylamino groups wherein each alkyl group is the same or different and each is an alkyl group having from 1 to 20 carbon atoms, monoarylamino groups wherein the aryl group is optionally substituted, diarylamino groups wherein each aryl group is the same or different and is optionally substituted and hydroxyl groups; said compound that reacts with said organozinc halide of formula R—ZnX being an imine of formula (II):

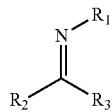 (II)
wherein $R_1$, $R_2$ and $R_3$ are as defined above; and
the organozinc halide of formula R—ZnX is a group of formula (III):
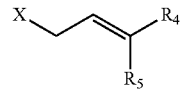 (III)
wherein $R_4$ and $R_5$ are as defined above and X is bromine or iodine.
* * * * *